United States Patent
Eliaz (10) Patent No.: US 10,828,413 B2
(45) Date of Patent: Nov. 10, 2020

(54) PATIENT SELECTIVE APHERESIS

(71) Applicant: ELIAZ THERAPEUTICS, INC., Sebastopol, CA (US)

(72) Inventor: Isaac Eliaz, Sebastopol, CA (US)

(73) Assignee: ELIAZ THERAPEUTICS, INC., Sebastopol, CA (US)

( * ) Notice: Subject to any disclaimer, the term of this patent is extended or adjusted under 35 U.S.C. 154(b) by 879 days.

(21) Appl. No.: 15/081,978

(22) Filed: Mar. 28, 2016

(65) Prior Publication Data
US 2016/0279314 A1    Sep. 29, 2016

Related U.S. Application Data

(60) Provisional application No. 62/139,026, filed on Mar. 27, 2015.

(51) Int. Cl.
   *A61M 1/34* (2006.01)
   *A61M 1/36* (2006.01)

(52) U.S. Cl.
   CPC ............ *A61M 1/3472* (2013.01); *A61M 1/34* (2013.01); *A61M 1/3486* (2014.02); *A61M 1/3679* (2013.01); *A61M 1/3681* (2013.01); *A61M 1/3683* (2014.02); *A61M 2205/053* (2013.01); *A61M 2205/75* (2013.01)

(58) Field of Classification Search
   CPC .......... A61M 1/3681; A61M 2205/053; A61M 1/3486; A61M 1/3679; A61M 2205/75; A61M 1/34; A61M 1/3472; A61M 1/029
   See application file for complete search history.

(56) References Cited

U.S. PATENT DOCUMENTS

| | | | | |
|---|---|---|---|---|
| 6,916,303 B2 * | 7/2005 | Tsuchida | ............... | A61K 31/045 604/4.01 |
| 7,850,634 B2 * | 12/2010 | Briggs | ............... | A61K 41/0066 604/6.08 |
| 9,888,673 B2 * | 2/2018 | Hering | ............... | A61K 39/395 |
| 2006/0186044 A1 * | 8/2006 | Nalesso | ............... | A61M 1/3472 210/645 |
| 2012/0164628 A1 * | 6/2012 | Duffin | ............... | G01N 33/54366 435/5 |
| 2014/0105997 A1 * | 4/2014 | Eliaz | ............... | A61M 1/3496 424/530 |
| 2015/0246169 A1 * | 9/2015 | Humes | ............... | A61M 1/3486 435/375 |
| 2016/0279314 A1 * | 9/2016 | Eliaz | ............... | A61M 1/3679 |
| 2016/0317734 A1 * | 11/2016 | Eliaz | ............... | A61M 1/3496 |
| 2017/0035955 A1 * | 2/2017 | Eliaz | ............... | A61M 1/3679 |

FOREIGN PATENT DOCUMENTS

WO   WO-2010033514 A1 *   3/2010   .......... A61M 1/3679

* cited by examiner

*Primary Examiner* — Leslie R Deak
(74) *Attorney, Agent, or Firm* — Steven B. Kelber (57) ABSTRACT

A system and method for the practice of apheresis employs modules in the system which can be selected for a particular patient to treat particular situations or combinations of difficulties. In one example, Gal-3 mediates a large number of body reactions, and is an effective protector of tumor microenvironments and the like, as well inflammation driver. Removal of Gal-3 may make antic-cancer treatments, like photopheresis and TNF administration more effective. Separate modules, such as one for photopheresis and one for TNF receptor removal, may be combined with a module for the reduction of Gal-3, to render the combination of treatments each more effective than if administered alone.

6 Claims, 3 Drawing Sheets

PATIENT SELECTIVE APHERESIS

PRIORITY DATA AND INCORPORATION BY REFERENCE

This application claims benefit of priority to U.S. Provisional Patent Application No. 62/139,026 filed Mar. 27, 2015 and PCT Patent Application Serial No: PCT/US14/38694 which are incorporated herein by reference in their entirety.

BACKGROUND OF THE INVENTION

Field of the Invention

The present invention relates to apparatus and methods employed to selectively treat agents in a mammal's blood outside of its body. In conjunction with such treatment, generally referred to as apheresis, agents can be added to improve or effect treatment of various disease conditions.

Statement of Related Cases

This application is related in character and function to U.S. Pat. No. 8,764,695 and U.S. patent application Ser. No. 14/141,509 filed Dec. 27, 2013, both to the same inventive entity of this application. Those two cases, the disclosures of which are incorporated herein-by-reference, are focused on the use of apheresis to selectively remove galectin-3 from a mammalian patient's bloodstream, to effect treatment of at least one of inflammation, fibrosis and cell proliferation. These patent publications focus on the use of selective agents, as opposed to general filter membranes and the like, to extract active or circulating galectin-3 from a patient's blood supply.

This application is also related to Patent Cooperation Treaty Application PCT/US14/38694 filed May 20, 2014. The entire disclosure of the related application is incorporated by reference herein as well. The later-filed case is directed to a apheresis device optimized to selectively remove galectin-3 and/or other blood components to better effect treatment of these patients in a variety of fields. The device features removable and replaceable "cartridges" or similar filters that allow for some optimization of the individual's treatment, thereby improving results because the removal and addition of contents is more closely tailored to the individual's needs.

SUMMARY OF THE INVENTION

Extended development of the apheresis treatment that originally focused on the removal of galectin-3 has revealed the value of apheresis in the treatment of a variety of mammalian situations that are not necessarily limited to galectin-3 removal, or selective removal of galectin-3 at all. Indeed, galectins make up a family of compounds which mediate a wide variety of biological functions, including everything from inflammation to uterine implantation and multiple aspects of homeostasis. Galectin-1, galectin-3, galectin-9 are among those most widely focused on, but all of the galectins in a mammal may be targets for treatment. In this application, a target galectin, such as galectin-3, may typically be removed in the treatment that an agent inhibited or medicated by galectin-3 is addressed as unrelated technologies, such as 3D printing, cancer treatment strategies and more closely aligned technologies such as personalized medicine have grown and developed, the inventor has recognized that the synthesis of apheresis with these other technologies opens up new doors and avenues to treatment that have not been fully explored.

Apheresis is conventionally defined as the removal of blood from a donor, typically a mammal, and more specifically preferably a human, a companion animal or a commercial animal, which may include separation of blood components, followed by return of most of those components to the patient by retransfusing the whole blood back to the patient. In most apheresis devices and treatments, blood cells are separated from plasma initially, and the plasma is subsequently treated to at least remove a blood component before return to the individual. Blood cells, which typically entrain platelets and related blood components, may also be treated (or collected for specific purposes such as to provide donor material). By removing the blood and plasma from the body, treatment of a wide variety of conditions and disorders becomes simplified, without having to deal, at least initially, with natural responses and side effects, such as cytokine-triggered inflammation responses. Thus, an entire new range of therapies may be offered that would be otherwise frustrated or limited by natural body defenses if administered to the patient in vivo, including blocking agents, cytokines, antibodies and the like. Thus, the treatment method contemplated herein is ex vivo, blood is removed, and it, or if preferred components thereof, are treated, to remove compounds, to add agents, and to specifically modify compounds or modulate aspects of the internal environment, or to collect specific cell types, before returning the altered fluids to the patient to effect treatments made possible by those alterations. Both the treatment methods, and the devices to effect those treatments, are contemplated herein.

This invention recognizes that ultimately, a positive treatment effective in the amelioration of one disease state in one patient, e.g., a cancer therapy, may be best deployed to treat the same disease in a different patient slightly differently, to account for differences in the two patients that may be due to age, race, genetic and epigenetic viability, co-morbidities such as obesity, diabetes, lung function and circulatory condition, disease stage, concomitant therapies, etc. Where for instance treatment is preventive rather than therapeutic, such as an attempt to remove specific potential cancerous cells or the like, genetic or other determinants may vary individual to individual. It would be of value to develop a general treatment that could be optimized or personalized for each individual, without the substantial cost currently associated with current applications of "personalized medicine." By taking advantage of the localization of the blood outside of the patient's body provided for by apheresis, a whole host of patient-specific modifications can be practiced. Many of these strategies are enhanced by being conducted ex vivo, so that body chemistry issues can be dealt with more selectively, or avoided.

Broadly stated, the invention calls for the adoption of an apheresis strategy specific to the individual. This includes the opportunity to deploy apheresis wherein apheresis may be used as a control device to make adjustments outside of the body instead of inside the body, where the inflammatory response is much more difficult to control as in the case of the selective removal of galectin-3 ("Gal-3"), as described in the aforementioned patents and applications. This could involve pre-treatment diagnostic to determine the serum level of Gal-3 in the patient, so as to identify the number of filters or cartridges required to remove the necessary amount. ("Gal-3" as used herein refers to circulating Gal-3 able to bind to receptors and molecules. Gal-3 exists in at least two, possibly three, forms, one of which is pentomeric and one which may be monomeric, but a dimer is also possible. It may also be bound by several polysaccharides. Gal-3 as used herein refers to all these forms.) It might further involve therapeutic or preventive diagnosis to prescribe agents or additives best added to the patient's bloodstream before return to the body, for instance, cytokines or altered cells, pharmaceuticals or natural agents, etc. for, e.g., a particular cancer therapy. This would include agents added in vivo before, during and after the apheresis process. There is no one target or single strategy that must be pursued. Instead, applicant identifies a list of potential strategies that might be pursued.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE INVENTION

This invention introduces a new method of addressing disabilities and conditions with interrelated strategies that improve the effectiveness of each strategy by reducing or eliminating other body systems and in vivo responses which tend to limit the effectiveness of conventional remedies. As only one example, a variety of medications and treatments are known to address excessive inflammation. Many are of limited effectiveness because of the mammalian tendency to induce inflammation for a variety of reasons. One of the compounds mediating inflammation is Gal-3. A conventional strategy to address inflammation may be made more effective by combining it with Gal-3 removal. Other treatments, which may be made more effective by reducing Gal-3 are disclosed. Gal-3 is an essential lectin expressed by the mammalian system, however, and cannot be blocked entirely without morbidity and mortality. A system which reduces Gal-3 concentrations while simultaneously administering other treatments (either removal or addition of other agents) ordinarily countered by effects mediated by Gal-3 in the body would be of value in this one example. Other examples abound. Thus the invention is a method for treatment, and a system for treatment, which relies on apheresis, conducted through a system which withdraws a patient's blood, optionally separates it into cellular and plasma components, and treats both as required in separate, interchangeable modules the function of which is dictated by the individual patient's needs. A new form of "personalized medicine" which makes use of a number of interchangeable modules adapted for a particular patient's needs is provided.
Summary of New Apheresis Strategies Strategic removal/modulation of multiple classes of bioactive compounds by using a variety of specific and/or non-specific filters.

Therapeutic control of levels of factors related and unrelated to removal of Gal-3.

Modulation of any bioactive compound that can contribute to the pathogenesis of any disease with utilization of the appropriate filters.

Treatment individualized for patient as well as each treatment optimized in relation to the individual's entire treatment program.

Use of apheresis as a stand-alone therapy or in combination or sequence with other pharmaceuticals, natural compounds, botanicals, nutrients, vaccines, photosensitizing agents, immune cell therapies, oxygen or oxidative therapies, ultraviolet or other electromagnetic therapies, heat therapies, chemotherapy, radiation, and surgical procedures with the aim of enhancing effects, synergizing treatments, reducing side effects and required dosages, and limiting longer term sequellae.

Use of apheresis in the acute setting to rapidly modify damaging internal pathophysiological processes as well as provide for rapid administration of specific therapies.

Use of apheresis in a preventive manner for conditions such as diabetes that are caused by overreaction of the body to the presence of viral infection, etc.

Use of apheresis as a periodic treatment for patients at high risk of cancer metastasis or recurrence by removing factors that increase risk and/or promote and/or enhance cancer growth, and/or enhance cancer resistance, example being growth factors such as VEGF, EGFR, TGF-Beta, etc.

Use of apheresis as a periodic treatment for a wide range of chronic conditions, such as autoimmune conditions for which control rather than cure is the goal, to prevent exacerbations (which can be life-threatening in some cases), and limit progression such as in chronic kidney disease, rheumatoid arthritis, etc.

Use of this new apheresis capability to develop/and use in conjunction with existing immune therapies (ability to collect various immune cell components, modulate in various ways by adding compounds, removal of compounds, multiplying the cells, etc.), (such as CAR-T genetically engineered cell therapy).

Development of Circulating Tumor Cell (CTC) therapies by collecting CTC's for both diagnostic and therapeutic purposes.

Development of and in conjunction with stem cell therapies, dendritic cell therapies, synthetic antibody mimics, immune checkpoint therapies, etc.

Traditionally, apheresis has been used to selectively remove a very few classes of agents or compounds. In the prior art, in general, molecular filters were provided to exclude a whole class of molecules that cannot pass through a specific molecular sieve—generally referred to as molecular weight range exclusion. U.S. Pat. No. 3,625,212, Rosenberg and U.S. Patent Publication No. 2006/0129082, Rozga are examples of this technique. It is not necessary, a priori, to exclude an entire class or molecular weight range to make effective use of apheresis. Antigens, antibodies, and a variety of targeted binding agents, generally exposed to the passage of blood or plasma within the apheresis device, as disclosed in pending PCT Application No. PCT/US14/38694 filed May 20, 2014, can be employed to selectively remove one or more specific types or classes of target compounds. Thus, this invention embraces a wide variety of apheresis removal strategies. Throughout this application the term mammal is used to address particularly humans, but may also embrace commercial mammals (pigs, cows, horses, etc.) as well as companion animals (dogs and cats, primarily). A few aspects of these are set forth below.

Compounds for Removal Using the Apheresis Process and Device for this Invention Include
- Cytokines, especially inflammatory cytokines
- Cytokine receptors
- Gal-s
- Other Lectins
- Growth factors
- Growth factor receptors
- Other growth factors
- Inflammatory factor receptors, an example being TNF Alpha receptors.
- Inflammatory, compounds, precursors, metabolites, etc.
- Tumor markers
- Endopeptidase Metzincin superfamily
- Tyrosine kinases
- Other proteins involved in cell migration and metastasis
- Other proteins involved in inflammation, fibrosis, and degenerative diseases including
- Advanced glycation end products,
- Beta amyloid, alpha synuclein and others involved in neurodegenerative diseases
- Other proteins that can bind to essential nutrients, or can block essential physiological processes and endocrine processes.
- Immune complexes
- Antibodies, examples include anti-DNA antibodies, anti-ganglioside antibodies and other antibodies to both internal tissues and pathogenic organisms.
- Immunoglobulins of the different classes—IgG, IgM, IgA, IgE
- Antigens
- Cryoglobulin
- Rheumatoid factor
- Angiogenic factors such as polypeptides
- Others including mycotoxins, viruses, bacteria, parasites and their toxins.
- Mast cells
- Amyloid beta(40) and amyloid beta(42)
- Antibodies to beta cells
- Circulating tumor cells
- Heavy metals and toxins a wide array of chemicals including pesticides, dioxin, PCB's, BPA and other plasticizers, etc.—both water soluble and fat soluble toxins.
- Pro-inflammatory factors
- Hormones and hormonal modulators
- Neurotransmitters and neurotransmitters modulators As noted above, the invention embraces not only removal of specific targets or compounds, but addition of specific compounds to the plasma or blood cells before return of the same to the patient's body. Often an addition in this fashion allows drugs or other agents to be added without further issues of patient compliance, without addressing questions of interference, reduced absorption, bioavailability or limited tolerance due to digestive tract kinetics or side effects, or binding compounds in the patient's circulation, and the like. In addition, by adding agents to the blood stream while conducting apheresis to remove agents, a highly personalized, sequential and optimized program of treatment can be effected through one step at one time, rather than following a standard protocol of one treatment regimen for every patient, or requiring patients to travel to multiple centers to receive multiple treatments. Often, agent addition can be balanced or selected to complement other agent addition, or blood borne compound removal through apheresis. A few of the agents that may be effectively removed through the use of this invention are described above. A few that may be selectively added are listed below. These are typically bioactive compounds that are added to achieve specific treatment goals either as stand-alone therapy or in conjunction/sequencing with other treatments (such as chemotherapy) and/or integrative therapies as described above.

Addition of Bioactive Compounds
- Recombinant Cytokines (that are being used as drugs)
- Cytokines
- Angiostatic proteins
- Oxygen therapies
- Stem cell therapies
- Immune cell therapies
- Hematopoietic cells of all kinds—B, T, etc.
- Attenuated and/or modified and/or enhance cells, such as T cells, B cells, macrophage, NK Cells, etc.
- Dendritic cell therapies
- Anti-fungal/anti-bacterial/anti-viral cytotoxic therapies
- Heat shock proteins
- Survivin
- Immunoglobulin
- Anti-CD20 antibody
- Lymphocyte depleting antibody
- Other immune stimulating factors
- Agents for disrupting biofilm
- Growth factors of various categories.
- Anti-oxidants
- Mineral, vitamins, nutrients, botanicals, proteins, amino acids.
- Detoxification support agents, examples being Glutathione, Taurine
- Chelating compounds such as EDTA, DMPS, DMSA, Tetrathiomolybdate (TM), etc
- Pharmaceutical agents of different kinds, example being chemotherapeutic agents, biological agents, hormonal agents, etc.

The invention is more than a list of compounds that may be effectively selected for addition or targeted for removal using the apheresis device of the claimed invention. It is a new approach to apheresis, including modulation of either the plasma and/or solid components of blood, or treatment of whole blood without separation, (without addition of either donor or artificial plasma) that is based on the idea that each individual can benefit from a treatment model and protocol that is tailored for the individual. In some cases, it might amount to no more than some diagnostic testing to determine appropriate levels of the target compounds, which permit accurate determination of the number and type of cartridges or filters the plasma should pass through, or the concentration of the additives to be introduced prior to retransfusion. In other cases, however, where the targets and/or additives are specific, or require a particular combination for a particular individual, it may be advantageous to design specific filter cartridges for that individual. One example is the selective removal of cells reflecting a genetic mutation in an individual, or harvesting stem cells bearing a particular signature for modification for later return to the individual to achieve tissue growth or removal or separation of cells for reintroduction with various immune therapy applications, etc.

In order to achieve the type of particularized treatment protocols called for by this invention, it may be necessary to formulate individualized columns or cartridges which may then be switched in and out of the general apheresis device, as described in the referenced patent application PCT/US14/38694 filed May 20, 2014. Indeed, while some therapies may be acute or one time only, for those patient's with a persistent condition or disease state—cancer, auto-immune diseases and the like, this invention allows preparation of an "ordered" set of filters to have on hand at facility proximal to the patient. This reduces costs and delays, and removes some of the anxiety associated with treatment. This opens up a variety of new designs and strategies for apheresis filter or column development not previously practicable. For instance, in prior art devices, a "one size fits all" approach generally required a molecular sieve strategy. In the new invention, even if patient one, for example, requires removal of Gal-3 and an auto-immune associated antibody, and patient 2 requires removal of Gal-3 and an inflammation-associated cytokine, they both require the Gal-3 removal filter, and wind up reducing the per patient cost of design/development/manufacture of that common module then each has a specific filter or column prepared for removal of the component, which is specific to them. By sharing costs where possible, and using new low cost technologies to make individualized patient care practical, new treatment modalities are possible. A variety of strategies for column construction are identified below, which make use of new technologies, such as 3D printing of columns and capture agents, such as antibodies, peptides, antibody fragments, aptamers, chemicals, antigens or derivatives, as well as the ability to tailor treatment of a particular individual. Some of these are identified below:

Column Development Strategies
  Pre-made columns based on a variety of technologies
  Custom columns using basic materials that are FDA approved for safety
  Use of 3 D Printing technology particularly for custom columns with patient specific matrices as well as for other more generalized column structures
Column Use for Apheresis Procedure
  Choice of column (s), number of columns, order of sequence
  Timing Pretreatment, during other treatments, post treatments
Columns Designed for Processing of Various Blood Components
  Use of whole blood
  Use of plasma
  Use of separated solid blood components (cells, larger proteins, etc.)
  Use of separators for specific cell populations Clearly then, the new approach to preventative and therapeutic treatment made possible by this invention's system may be targeted to the individual and adapted to the individual's needs, but relies in part on apparatus and practices and strategies applicable to entire groups and classes of patients. A "column" is a traditional term to refer to a section of the device that may be switched in and out. Examples include a passage lined with antibodies that bind Gal-3 or a passage lined with antibodies that bind TNF Alpha, etc. Applicant recognizes that the actual design of the passageways, as well as the agents that bind target compounds, will change as personalized treatment comes to the fore (for example, targets that are more difficult to bind might require a more tortuous path to extend the time they are in contact with binding agents). New applicable materials and methods for column construction will become available. In a preferred embodiment, multiple different "columns" are designed and switched out as the patient responds to treatments. Thus, the filters or removal columns and modules become interchangeable, and the pattern and number of such "columns" can be varied from patient to patient or for the same patient at different times using the same machine. For example, in a patient needing removal of only one target compound, several "column" spacings might be occupied by straight unlined tubing, where the same machine when used for another patient might exhibit 3 or 4 or more "columns" placed in sequence. Ultimately, the system becomes one where there is a basic machine, with spaces for three or four or five "columns" or filter packs. Each module site may be occupied, or there may be capability for bypass using appropriate tubing and connectors when not occupied by an active column. In such circumstances, not only column design and character, but sequencing is part of the individualization of treatment. Different issues to take into consideration in developing patient strategies are set forth below:

Basic Concepts
  Columns
    Pre-made columns: Columns remove specific components via a variety of potential technologies including selective removal, size exclusion, non-selective removal, receptor binding, antibody binding, precipitation, charge based, size exclusion, electromagnetic, etc.
    Custom columns: Obtain approval for the basic materials/FDA approved safe materials, and/or materials that are inert and will not cause an adverse reaction in the binding process.
      Custom features made to order based on individualized assessment, which could include analysis of: tumor genetics/phenotype and membrane receptors, levels of elevated blood borne cancer and inflammation promoting factors (CIPFs), immunological factors, etc. described more fully below.
      3D printing technology and other technologies could include patient specific tissue matrices with embedded components both biological and electrical such as sensors to detect concentrations, so that the flow through the columns and concentrations of agents, cellular components and CIPFs could be monitored and modulated appropriately. Custom columns/filters developed that would be suitable for treating any biological condition including inflammatory, degenerative, allergic, autoimmune, infectious, fibrotic and neoplastic.
Sequencing
  Of Columns
    choices of columns
    numbers of columns
    order of sequence
  Of Timing
    Apheresis pre-treatment (such as prior to chemotherapy) or during treatment (for example during chemotherapy)
    Post treatment
Plasma Separation as Well as Whole Blood Filtering Systems
  With use of whole blood, once separated, the two components can be worked with simultaneously and then reunited, or different procedures can be accomplished using one or the other (i.e., meaning plasma, whole blood, or blood cellular components) depending on the goal of treatment.
  With use of unseparated whole blood, specific cell types can be removed or treated as well as modulation of blood borne proteins and other factors. Whole blood that has been cleaned using plasma apheresis has lipids and inflammatory compounds removed which would enhance the detection of CTC's, immune cells, etc., and would thus be a preliminary treatment to further apheresis applications as described in this document.

Development of Columns Based on 3D Technology

This new technology is just beginning to reveal its capabilities for constructing scaffolding, matrices, living tissues, etc. that can be envisioned as material for column construction for specific purposes. These columns would be designed for a variety of complex functional capabilities with examples further described below.

- Optimized for removal of one or more specific factors either in combination with Gal-3 removal or independent, with option to use multiple filters in a cascade to remove multiple compounds.
- 3D printing of receptors, matrix embedded compounds with high affinity for specific factors. For example, the printer could print a column that contains receptors for growth factors, signaling factors, etc., including but not limited to VEGF, EGFR, TGF beta family, interleukins, fibroblast growth factors, neurotrophic factors, cancer cell receptors (CD family) receptors for various galectins, survivin, etc.
- 3D Printing of specific binding sites for individualized columns based on:
  Laboratory testing
  Profiles of tumor expression
  Genomic analysis of the tumor,
  Genomic analysis of the individual.
  Analysis of the tumor cell membrane characteristics and protein expression
- Materials used will be FDA approved as safe, etc, or inert compounds that do not interact.
- Filter construction, either using 3D printing or other design may bind or attract based on a number of different technologies including physiological binding antigen/antibody, receptor binding (for example EGFR), electric charge, size exclusion, etc.
- Incorporation of synthetic antibody mimics (SyAMs) and fragments (e.g., scFv, Fab, Fab', Fc) which attach themselves simultaneously to disease cells and disease-fighting cells. Included within this approach is the addition of various peptide fragments such as Fab, FC, etc.
- Potential for incorporation of electrical sensor technology which could be used for identifying particular molecules or sensing levels of molecules.
- Columns might include UV, laser, or other light capability, (existing photopheresis technology), or magnetic fields.
- UV light, laser, light sources and energy attenuation devices (EMF's and other energy sources) can be integrated in to the extracorporeal apheresis procedure, in all stages: Whole blood, separated cells in general and subpopulations, plasma, joined blood (cells and plasma) both separation. The goal here is to make it specific to source of energy and frequency, and to make it timing specific as well.
- Electromagnetic therapy could be in the form of a single column or embedded in the matrix of a column, such as one that could also bind CTC's, bacteria, viruses, spirochetes.
- For example: a matrix that would attract and bind specific organisms, along with electronic sensing imbedding to monitor density. UV or other therapy could then be turned on based on this to destroy accumulated organisms.
  This could be combined with a column that could be made to bind specific compounds that act as growth promoting substrates for infectious organisms.
- Photosensitizing medications can be incorporated.
- Cancer cells could also be targeted with this type of technology.
  3D Matrix could contain binders for CTC as a way to remove, or capture these cells to introduce T-cells or other immune cells reactive to the tumor for activation, right in the column instead of removing from the body altogether and reintroducing as is done currently.
- Alternatively, personalized materials may be harvested and cultured, but reintroduced in the apheresis process to ensure reduced side effects and increased efficacy. For example, by reducing pro inflammatory cytokines and compounds and adding other compounds that will enhance the therapeutic effect or improve the delivery to the target tissue, apheresis can be used to improve the effectiveness of other therapies.
- Apheresis can be used as a purely diagnostic exercise (As one example, CTC's might be bound and held on a 3D scaffolding that can be separated from the patient and used to test chemo drugs and other therapies for efficacy).
- Compounds can be run through a column where particular cell components or other factors have been bound, with the purpose to "unglue bound components at a strategic point for the next step in the therapy.
- The process could be continuous, or could be an adjunctive procedure which could be another part of the machine that would siphon a certain quantity of whole blood, and cycling it thru a column over some hours with heparin where the cells are cultured in the column and returned, so you can have a process where you are culturing a treatment on one side and you are removing the inflammatory compounds at the same time
- Using 3D technologies to construct custom scaffolding on which living cells can be cultured producing tissue matrices such as connective tissue (using NAG or other compounds), which can attract binding by Lyme spirochetes or other infectious agents, making the spirochetes accessible for therapies including T-cell stimulation therapies, allowing for removal or for direct application of light or other cytotoxic therapies. Tissues could be made homologous to the patient and printed on columns for various uses such as above
- Detection of subpopulations of cells for example RBC's that are infected with *Plasmodium falciparum* (Malaria), *Babesia* spp. (Babesiosis), and alike, allowing for elective removal of the infected cells without causing anemia and too big of depletion of red blood cells. Subpopulations of cells can be targeted.
- Cells can be grown into a type of matrix or tissue that can have other technologies imbedded in it such as combination of the tissue with electronics, sensors, etc.
- Electronic sensing capabilities can be used for a multitude of purposes in terms of sensing levels of specific compounds passing through the filter, or the concentration of bound compounds, or density of particular cell types bound to filters, or microorganisms. This can allow for timing of the various components of the particular procedure.

Immune Therapies and Circulating Tumor Cell Therapies

To develop new technology for advanced immune therapy based on filters and devices such as centrifugation procedures with the capability to collect various relevant cell types including circulating tumor cells (CTCs), T-cells, B-cells, macrophages, monocytes, dendritic cells, and other emergent immune modulating concepts are listed below.

CTC collection for therapeutic and diagnostic purposes.

Cells could be analyzed ex-vivo for genetic and membrane specific receptors, proteins, as well as their secretion of cytokines and other factors such as IL-6 and IL-8.

For example, if we find that a person's CTC's have a particular receptor, e.g., CD4, we can target them with binders for this receptor.

CD receptor family, CCR receptor family.

We can create a custom column containing one or multiple binders for patient specific CTC characteristics.

Can harvest CTC's and hold them on a 3D scaffolding that can be separated from the patient and used to test chemo drugs and other therapies for efficacy. (Organovo).

Patient specific therapies based on the results would be developed.

Incorporation of Targeted Stem Cell Therapies

Binding of CTC's and or T/B cells for purposes of "educating" the immune system is now possible. Identifying Cancer stem cells (CSCs) and removing them specifically, or creating therapies targeting the receptors in the CSC's promoting therapies each made more effective by their combination. These are among the principal reasons for recurrences and resistance to therapy.

The bound agents and materials can be reinfused at a later date. Alternatively they could be co-cultured on a column with whole blood being circulated. This would take a certain amount of time. Example: you have an antigen specific to the cancer cells, and you have B cells co-cultured, then you run heparin or an appropriate agent that will release the cells at a certain point. The B cell attaches to the receptor and the antibody or FC fragment gets stimulated, then the potentiated B cells are re-infused in a closed system.

Using apheresis to change the density of the antibodies to control the rate of exposure and the rate of the reaction Examples of Targeted Stem Cell Therapies that could be Incorporated into this Technology:

CAR-T: T-cells genetically engineered to produce special receptors on their surface called chimeric antigen receptors (CARs). CARs, proteins that allow the T cells to recognize a specific protein (antigen) on tumor cells.

Engineering stem cells to secrete cancer-killing cytotoxins. These stem cells are placed inside the tumor and destroy the tumor from within. The cytotoxins can be targeted to cells with specific receptors such as epidermal growth factor or IL-13 receptor alpha 2 (IL13RA2) found in many brain tumors (this work is in process).

Dendritic cell therapy

Targeting activation and regulation of T cells

Oncolytic virus vaccines

Adoptive T cell therapies

Collection, identification, and selective removal of the subpopulation of immune cells that are excreting specific cytokines (for example inflammatory IL-6 and IL-8).

Incorporation of synthetic antibody mimics (SyAMs) either as a therapy in itself or incorporated into the filter technology.

SyAMs work first by recognizing cancer cells and binding with a specific protein on their surface. Next, they also bind with a receptor on an immune cell. This induces a targeted response that leads to the destruction of the cancer cell.

This invention not only opens up new opportunities to personalize treatments for a specific mammalian patient but allows the complementing of other treatments the patient may be receiving. Thus, often certain treatments will aggravate or unnecessarily suppress natural body responses, like inflammation or stomach or bowel upset, due to a cascade of conditions or comorbidities that are mediated by factors other than the one directly involved in the patient's condition or therapy. Other phenomena that may be associated with treatments involving surgery and the like may include the development or aggravation of fibroses, or upregulation of growth factors, increasing risk of metastasis, etc. Such combined therapy approaches will require consultation and comprehensive monitoring, but may vastly increase the effectiveness of traditional treatments. Accordingly, part of this invention is employing apheresis to remove agents or conditions that that might otherwise interfere with other treatments. Some of these strategies include a variety of uses of apheresis and selective targeted removal associated with other treatments including the following concepts and approaches:

Use Apheresis Technology to therapeutically control levels of circulating CIPFs and immune modulating factors, all of which play a role in different conditions and could be removed or modulated at different stages, both related and unrelated to removal of Gal-3 based on the patient and the condition being treated. Apheresis becomes like a control device where you make the adjustments outside of the body instead of inside the body where the inflammatory response can be much more difficult to control.

Regulate the inflammatory response to reduce side effects of standard therapies as well as emerging targeted treatments, enhance effectiveness, reduce side-effect induced treatment interruptions, and allow for lower, more tolerable doses of agents used.

In preparation for, prior to, in conjunction with, and/or post-surgery, chemotherapy, pharmaceutical therapies, targeted therapies such as mAB, immune therapies, hormonal therapies, radiation, hyperthermia, photodynamic therapy, and other integrative therapies using botanicals, nutrients, etc.

Reduce pro-metastatic inflammation and the upregulation of growth/repair factors potential for release and growth stimulation of tumor cells post-surgery.

Removal of CTC's pre and/or post-surgery so you don't let the body induce a metastatic process especially with tumors that spread hematologically.

Reduce post treatment fibrosis secondary to surgery and radiation.

As a result of chemical, pathological or chronic inflammatory insult to an organ or organs such as is the case with chronic kidney disease, liver diseases, lung diseases, cardiovascular diseases, and exposures to toxins such as pharmacological agents, mycotoxins, heavy metals, etc.

Reducing inflammatory compounds that protect the tumor cell environment from access by chemotherapeutic and immune stimulating agents.

Addition of other agents using sophisticated protocols in combination with columns, such as IV vitamin C, artesunate, ozone, honokiol and its derivatives, oxidative therapies, enzymes, heparin, other anti-viscosity agents, photosensitizing agents, pharmaceuticals, chelating agents, ultraviolet and other light and electromagnetic therapies, etc.

Reducing growth factors in the blood to enhance the effectiveness of growth factor inhibition therapies such as tyrosine kinase inhibitors, etc.

Agents specific for disrupting biofilm, the protective sheath that covers tumors, arteriosclerotic plaques, Lyme spirochetes, autoimmune processes, etc.

The invention further comprises introducing agents to provide a novel treatment for infectious diseases such as Lyme disease, for example, by using compounds that can cause an infectious organism, such as Lyme spirochetes, to move from tissue sequester sites into the bloodstream. This could be combined with aforementioned filter to simultaneously remove growth factors specific for the infectious organism as well as column matrices (which could be living tissues) that would attract said spirochetes for binding, followed by in column cytotoxic therapy, essentially sequestering the cytotoxic treatment from the patient's system, reducing systemic reactions and side effects.

Among the most intractable and devastating of diseases are a host of auto-immune diseases. The invention specifically contemplates using filter technology to create novel sequential strategies for addressing autoimmune diseases in a similar fashion. Many autoimmune processes occur in pockets, the body walls off sites of infection, the organisms create protective biofilm, creating an anaerobic and/or isolated environment that the immune system cannot access. This creates a chronic inflammatory locus which can develop into an autoimmune process which will stop when the area is exposed and treated.

Introduction of oxidizing agents once infectious sites have been accessed using anti-biofilm therapies. Example: manipulating myeloperoxidase, which is bound by heparin (and spikes during LDL apheresis) time release to enhance a specific antimicrobial therapy. May choose not to remove elevated Gal-3 and/or treat with inflammatory or oxidative compounds to enhance effect for infectious diseases while controlling other inflammatory cytokines.

Gal-3 could be retained during certain points of therapy for fighting infectious organisms due to its enhancing effect. It might be removed at the end of treatment to reduce inflammation produced by the process of antimicrobial therapies. Other galectins may be retained or removed at any stage as only a few examples, galectins 1 and 9 have been implicated in rejection syndrome, and in impregnation difficulties.

Introducing agents, such as growth factor inhibitors, or multi-drug resistance (MDR) inhibitors along with standardized therapy or just prior to or following to enhance effectiveness of anticancer therapies such as chemotherapy. These agents could be introduced at key points during or following apheresis.

Remove specific growth factors while retaining other's needed to balance the reaction.

Increase the effectiveness of immune therapies by reducing inflammation, treatment side effects and improve the response by allowing the cells to get to the target tissue much easier.

Incorporating new classes of immune therapies such as targeted oncovirus, T and B cell therapies, dendritic cell therapies, stem cells, nanotechnologies for targeting tumor cells and tumor macrophages, etc., immune modulation agents, such as PD-1/PD-L1 inhibitors (antibodies that allow the immune system to attack tumor by blocking the pathway that paralyzes the immune response).

To use instead of/or reduce the dosages of existing pharmaceutical treatment for diseases such as autoimmune conditions by binding to inhibitory proteins, antigens and circulating immune complexes that drive tissue damage. Therapy could reduce or eliminate the need for immune-suppressive therapies with their negative long term side effects.

As a periodic treatment for patients at high risk for metastasis or recurrence to remove both inflammatory and hyperviscosity factors and CTC's that may be putting them at risk.

The use of the apheresis invention disclosed herein has been described above in the context of individualized treatment of mammalian and human patients, and as an element of a combination of therapies for such patients. Thus, apheresis may be effective on its own in addressing or reversing a variety of disease states. This invention embraces a variety of strategies to personalize such treatment, to tailor it for the needs and character of the individual patient. It may also be effectively used to promote the effectiveness of other therapies, such as cancer treatment and the like. It may also be used, as discussed above, to remove factors that would otherwise inhibit the effectiveness of more conventional strategies, or make it possible to enable administration of those strategies without profound risk, such as the risk of fibroses or tumor metastases. It is not limited, however, to therapeutic or clinical intervention. It finds application in pre-clinical or pre-therapeutic situations, or when the patient is not yet symptomatic. Some of these pre-clinical applications include:

Removal of inflammatory compounds, immune complexes and antibodies in advance of the overt clinical manifestation of autoimmune diseases.

Removal of inflammatory and autoimmune complexes in other preclinical situations, and specifically in IDDM, or Type I diabetes. Given prescreening in high risk for Type I Diabetes and screening for antibodies against langerhans cells (Beta islet cells of the pancreas) apheresis may be used pre-clinically to prevent development of diabetes. Gal-3 is implicated in the inflammatory process in diabetes. Gal-3 removal coupled with removal of other complicating factors may suppress the disease or its most debilitating symptoms.

Remove the antibodies via apheresis. There is elevation in these antibodies long before type I diabetes sets in.

Couple this with the various anti-inflammatory therapies discussed above.

Remove the viruses that are implicated in the initiation via apheresis.

If the typical immune inflammatory response is avoided using apheresis, diabetes can be prevented.

This strategy will also apply to other autoimmune conditions, myopathies, neurodegenerative diseases, etc. such as ALS, MS, Alzheimer's, Parkinson's and other degenerative diseases that are devastating in their outcome and extremely expensive to treat once established.

While the use of therapeutic apheresis is already known for some of these diseases, such as Crohn's disease, neuromuscular conditions, etc. to the best of our knowledge, it has not been used in a pre-clinical or pre-symptomatic situation, to prevent development of this disease condition.

Fundamentally, this invention opens new opportunities and avenues for the use of apheresis, which may include blood cell treatment, plasma treatment or both. It permits the personalization of treatment without extraordinary expense by deploying a single device or apparatus that can be modified for individual treatment by the switching in and out of targeted columns or filters without the cost of development of a new machine for each major type of illness or condition. It allows for the simultaneous maintenance of conventional technologies that may otherwise be limited or prohibited because of responses due to removable targets. It makes apheresis of value in both clinical and pre-clinical settings. However apheresis is only as good as the effectiveness of the column(s) in removing the target compound or subject matter. The development of unique antibodies and binding partners for a universe of materials, and the ability to deliver or "print" these on a scaffold or supporting surface over which a patient's blood or plasma can be led, vastly expands the capabilities and applications that apheresis may be put to. We identify below only a handful of the types and categories of target compounds and subject matter that may be removed by the "personalized" apheresis of this invention. At least ten different very broad categories, as well as a "miscellaneous" category may be identified, as organized below: Many of these compounds are multifunctional and have complex physiological roles, with necessary regulatory functions in specific conditions and situations, while in other situations would have more pathogenic effects warranting removal.

Cytokines

A large group of soluble extracellular proteins or glycoproteins, key intercellular regulators and mobilizers.

Classes of Cytokines:
  Chemokines
    Homeostatic: are constitutively produced in certain tissues and are responsible for basal leukocyte migration. These include: CCL14, CCL19, CCL20, CCL21, CCL25, CCL27, CXCL12 and CXCL13. This classification is not strict; for example, CCL20 can act also as pro-inflammatory chemokine.
    Inflammatory: these are formed under pathological conditions (pro-inflammatory stimuli, such as IL-1, TNF-alpha, LPS, or viruses) and actively participate in the inflammatory response attracting immune cells to the site of inflammation. Examples are: CXCL-8, CCL2, CCL3, CCL4, CCL5, CCL11, CXCL10, CCL's, CXL's, CX3CL, XCL'S
  Interleukins-multiple subclasses (IL) and families some of which are proinflammatory
  Interferons (IFN)
  Lymphokines
  Tumor necrosis factor families (including TNF-alpha, -beta)
  Adipokines (adipocytokines): Cytokines secreted by adipose tissue.
    Leptin
    Adiponectin
    Apelin
    Chemerin
    Interleukin-6 (IL-6)
    Monocyte chemotactic protein-1 (MCP-1)
    Plasminogen activator inhibitor-1 (PAI-1)
    Retinol binding protein 4 (RBP4)
    Tumor necrosis factor-alpha (TNF-alpha)
    Visfatin
Other Cytokine Related Targets
  Receptors: removal increases response at target tissue.
    Chemokine Receptors
      CCL13 (MCP4), CCR1, CCR2, CCR3, CCR4, CCR5, CCR6, CCR8, CX3CR1, CXCR1 (IL8RA), CXCR2 (IL8RB).
    Interleukin Receptors
      IL10RA, IL10RB, IL1R1, IL5RA (CD125), IL9R.
    Other Cytokine Receptors
      TNFRSF11B (OPG).
    Galectins
    Lectins
Growth Factors:
  Epidermal Growth Factor Receptor (EGFR)
  Epidermal Growth Factor (a kinase)
  Activator Protein-1 (AP-1)
  Vascular endothelial growth factor (VEGF) family
  Hepatocyte growth factor (HGF)
  Transforming growth factor alpha family and beta family
  Basic fibroblast growth factor (bFGF) (-2)
  Tumor necrosis factor alpha (TNF alpha)
  Heparin binding epidermal growth factor
  Insulin-like growth factor (IGF) family including IGF 1, 2 Vascular adhesion molecule-1
  Endothelial intercellular adhesion molecule
Other Growth Factors Include:
  Adrenomedullin (AM)
  Angiopoietin (Ang)
  Autocrine motility factor
  Bone morphogenetic proteins (BMPs)
  Brain-derived neurotrophic factor (BDNF)
  Erythropoietin (EPO)
  Glial cell line-derived neurotrophic factor (GDNF)
  Granulocyte colony-stimulating factor (G-CSF)
  Granulocyte macrophage colony-stimulating factor (GM-CSF)
  Growth differentiation factor-9 (GDF9)
  Erythropoietin (EPO)
  Healing factor
  Nagalase
  Hepatoma-derived growth factor (HDGF)
  Sonic Hedgehog (polypeptide-abnormal activation of the pathway probably leads to development of disease through transformation of adult stem cells into cancer stem cells that give rise to the tumor)
  Interleukins: 1-7
  Keratinocyte growth factor (KGF)
  Migration-stimulating factor (MSF)
  Myostatin (GDF-8)
  Nerve growth factor (NGF) and other neurotrophins
  Thrombopoietin (TPO)
  Wnt Signaling Pathway
  placental growth factor (PGF)
  Foetal Bovine Somatotrophin (FBS)
  Renalase-RNLS-Anti-apoptotic survival factor
  Endothelins
  Ephrins
Tumor Markers: (biologically active)
  CEA (carcinoembyronic antigen)
  CA-125 (cancer antigen-125)
  CA-19-9 (cancer antigen)
  CA 15-3
  CA 27-29
  Prostatic Acid Phosphatase
  Prostate Specific Antigen (PSA), proPSA (p2PSA), freePSA
Endopeptidase Metzincin Superfamily.
  Matrix Metaloproteinases: most important class MMP Groups are the collagenases, the gelatinases, the stromelysins, and the membrane-type MMPs (MT-MMPs).
  Adamalysins, serralysins
  Astacins Collectively, these enzymes are capable of degrading all kinds of extracellular matrix proteins, but also can process a number of bioactive molecules. They are known to be involved in the cleavage of cell surface receptors, the release of apoptotic ligands (such as the FAS ligand), and chemokine/cytokine inactivation.[2] MMPs are also thought to play a major role on cell behaviors such as cell proliferation, migration (adhesion/dispersion), differentiation, angiogenesis, apoptosis, and host defense. There are a wide variety of MMPs, some are noted below.

Tyrosine Kinases:
  soluble fms-like tyrosine kinase-1 (sFlt-1), (elevated in preeclampsia)
  sVAP-1 (serum vascular adhesion protein-1)
  ICAM-1
  VACM-1
  Others Proteins involved in cell migration/metastasis: (some of these are newly discovered and are primarily intracellular, but may be shown in future studies to also be found in the circulatory system).
  DENND2B: DENND2B activates another protein in the cell called Rab13, which is an enzyme that promotes cell migration,
  RSK2: significantly increases cell migration in part by reducing integrin activation. Integrins play an important role in cell adhesion to their surrounding tissue and the migration of tumor cells to new locations in the body. RSK is active in both breast and prostate tumors, and promotes proliferation in these cells. It can also promote cell invasion and metastasis in head and neck cancers in addition to lung cancer and neuroblastoma.
  hnRNPM: helps launch a cascade of events that enables breast cancer cells to break away from the original tumor, penetrate the blood stream, invade another part of the body and form a new nodule of that tumor.
  HIF-1
  JMJD2C
  HIF-1 switches on the JMJD2C gene, stimulating production of the protein. HIF-1's presence also enables JMJD2C to bind to DNA at other HIF-1 target genes, and then loosen those DNA sections, enabling more HIF-1 to bind to the same sites and activate the target genes.
  NOS2: high levels of NOS2 are a predictor of poorer survival in patients with ER-negative breast tumors and to suggest that selective NOS2 inhibitors might be of benefit to these individuals. Inducible nitric oxide synthase (NOS2) is involved in wound healing, angiogenesis, and carcinogenesis.

Other Proteins and Proteases:
  Bcl-2 family
  Inhibitor of Apoptosis family (includes survivin)
  Cathepsin Family
    A, B, C, D, E, F, G, H, K, L1, L2, o, S, W, Z
    Integrins
    Antigens
    Antibodies
    Immune complexes
    Caspase family (most act intracellularly, but some are found in serum)
    Myeloperoxidase
  Angiogenic Polypeptides: (which may be listed elsewhere)
    Activator protein 1 (AP-1)
    Angiogenin (AG) and angiotropin (AT)
    Angiopoietin (APN)
    Basic fibroblast growth factor (bFGF)
    Cyclooxygenase (COX) and lipoxygenase (LOX)
    Granulocyte-colony stimulating factor (G-CSF)
    Hepatocyte growth factor (HGF)
    Insulin-like growth factors 1 and 2 (IGF-1 and -2)
    Interleukin-8 (IL-8)
    Nuclear factor kappa B (NF-kB)
    Placental growth factor (PGF)
    Platelet-derived endothelial cell growth factor (PD-ECGF)
    Platelet-derived growth factor (PDGF)
    Pleiotrophin (PTN)
    Proliferin Thrombospondin-1 (TSP-1)
    Transforming growth factor alpha (TGFα)
    Transforming growth factor beta (TGFβ)
    C Reactive Protein (CRP)
    Tumor necrosis factor alpha (TNFα) and TNFβ (has both pro and antiangiogenic roles) Vascular permeability factor (VPF)
  Others:
    Malondyaldehyde (MDA)
    2-thiobarbituric acid (TBA)
    Secretins
    Adenosine diphosphate (SDP), thrombin and other molecules that participate in platelet-tumor cell interaction.
    Tumor-derived platelet agonists, such as adenosine diphosphate (ADP) and thrombin, induce platelet activation, followed by the formation of heterotypic aggregates that protect tumor cells from immune attack and physical damage. Tissue factor expressed by tumor cells also leads to thrombin generation through the activation of the coagulation cascade that ultimately results in fibrin formation and platelet activation. These processes, among others, promote the development of venous thromboembolism in solid tumor and hematological malignancies.
    Fungus and/or their toxins—Mycotoxins
    Viruses
    Microbial agents—bacteria, viruses, fungus, helminths, parasites and their toxins Also as noted, apheresis as employed in this invention can be, but need not be, a "stand alone" treatment, even if not associated with some other treatment modality. Given the proper apheresis device, such as that set forth in PCT/US14/38694 filed May 20, 2014, there are important opportunities to supplement the blood of a patient without ever treating the patient's body, by adding agents to the blood or plasma stream ex vivo. The added agents can be cells or cell fragments or compounds harvested from the patient's body, altered and returned, or synthetic drugs or compounds or agents new to the patient, including a variety of natural agents, and everything in between. The point of addition is flexible, depending on the agent to be added, it may be added before, during or after the whole blood is otherwise treated in the system. Although it is clear that from the date of this writing onward, new potential agents to be added via the "return loop" of the apheresis device of this invention (that is, after the blood or plasma or both has passed through the columns or filters) some are specifically mentioned below:
  Addition of Cytokines during apheresis for various treatment protocols could include: (Some cytokines have been developed into protein therapeutics using recombinant DNA technology. Recombinant cytokines being used as drugs as of 2014 include):

Bone morphogenetic protein (BMP), used to treat bone-related conditions

Erythropoietin (EPO), used to treat anemia

Granulocyte colony-stimulating factor (G-CSF), used to treat neutropenia in cancer patients Granulocyte macrophage colony-stimulating factor (GM-CSF), used to treat neutropenia and fungal infections in cancer patients Interferon α, used to treat hepatitis C and multiple sclerosis Interferon beta, used to treat multiple sclerosis Interleukin 2 (IL-2), used to treat cancer.

Interleukin 11 (IL-11), used to treat thrombocytopenia in cancer patients.

Interferon γ, used to treat chronic granulomatous disease & osteopetrosis.

Addition of angiostatic proteins

Addition of factors in conjunction with chemotherapy

Addition of oxygen therapies including in conjunction with hyperbaric oxygen treatment Addition of bacterial and viral cytotoxic therapies Addition of anti microbials of all classes—anti viral, anti bacterial, and helmetic, anti parasitic.

Addition of Survivin
  Survivin is a strong T-cell-activating antigen, and clinical trials have already been initiated to prove its usefulness in the clinic.

Addition of Heat Shock Proteins (HSPs) as cancer vaccine adjuvant
  Given their role in antigen presentation, HSPs are useful as immunologic adjuvants in boosting the response to a vaccine. Furthermore, some researchers speculate that HSPs may be involved in binding protein fragments from dead malignant cells and presenting them to the immune system. Therefore HSPs may be useful for increasing the effectiveness of cancer vaccines. Extracellular located or membrane-bound HSPs mediate immunological functions. They can elicit an immune response modulated either by the adaptive or innate immune system. In cancer, most immune therapeutic approaches based on extracellular HSPs exploit their carrier function for immunogenic peptides.

Figure 1:
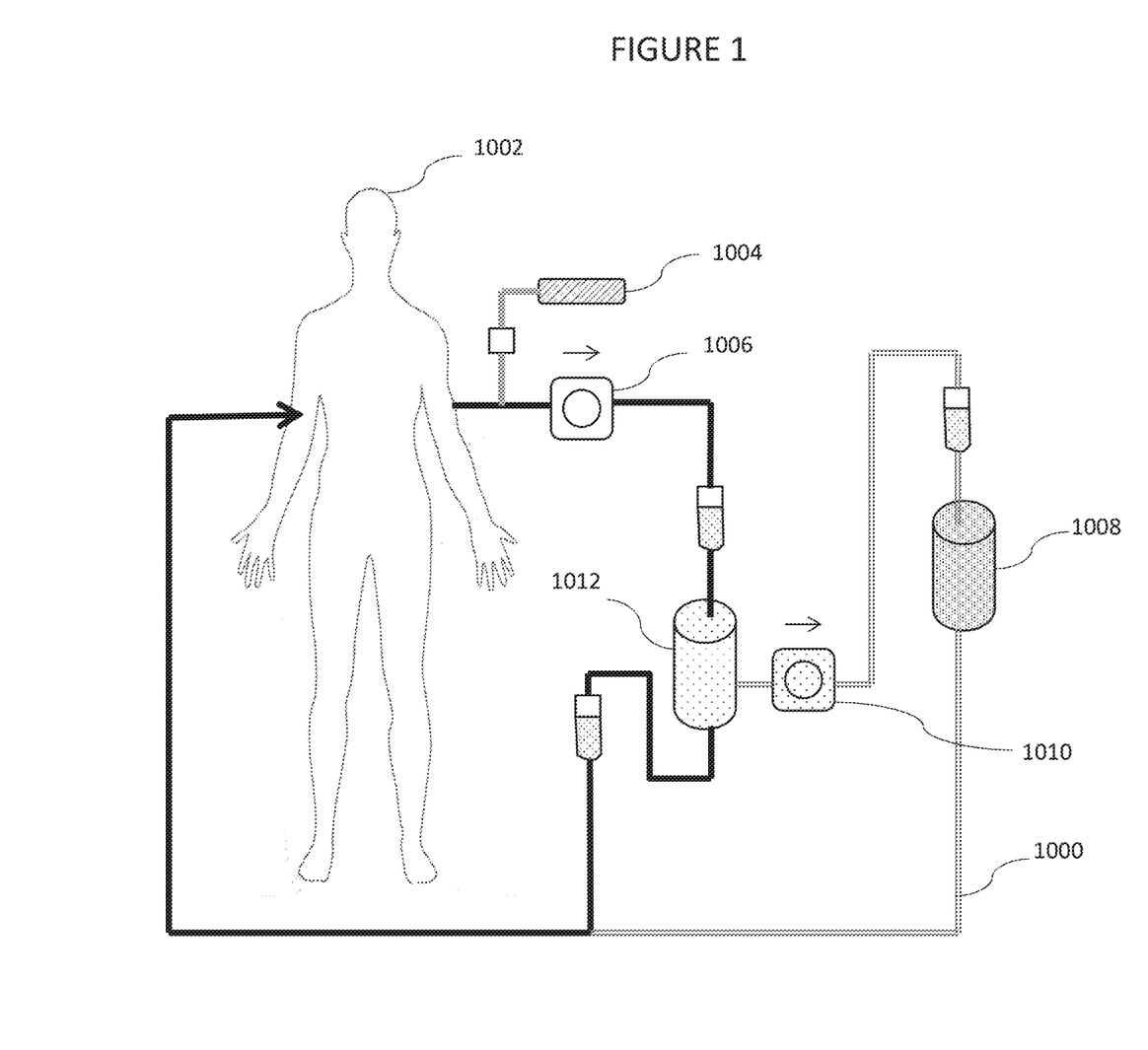
FIG. 1 is a broad schematic illustration of the device of this invention, reflecting separation of whole blood into blood and plasma, treatment of the plasma, return of the plasma to the blood component and restoration of the treated whole blood to the patient.
Figure 2:
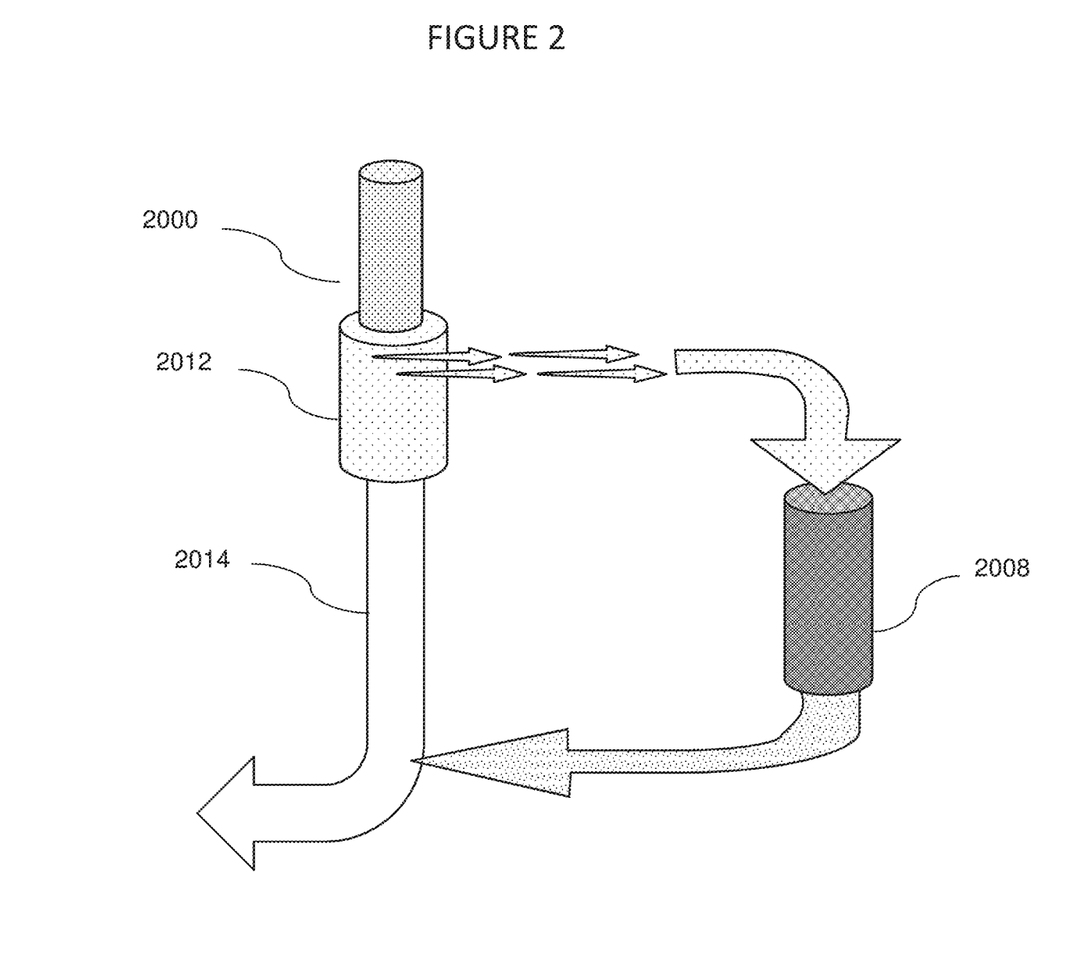
FIG. 2 is an illustration schematic of the portion of the device where plasma is separated out of the blood, (which can occur via one of several existing separation technologies) treated in at least one column and returned via a conduit to the blood and donor.

As noted above, Applicant's invention allows an unprecedented opportunity to combine therapies that reinforce each other. One of the principal achievements using this therapy is the selective removal of Gal-3. By employing plasmapheresis or apheresis to selectively remove Gal-3 (removal can be effected by removal from whole blood or from plasma following separation) by even a limited percentage (for instance, ten percent) a significant improvement in both acute and chronic inflammation can be achieved. But by removing the blood from the patient and providing a limited time opportunity to selectively impact other components of the blood, a variety of therapies which are interrelated in terms of action and target can be combined in time as well, improving effectiveness. In terms of the drawings provided, the blood in such an embodiment is withdrawn and pumped by pump 1006 from mammal 1002. If desired, it is separated at filter 1012 into blood components and plasma components, although the whole blood may be treated as one unit. The blood passes through module 1008. In this example, the module comprises an opening through which the blood or plasma is led which comprises a Gal-3 binding molecule the blood or plasma is exposed to. The molecule, an antibody, antibody fragment, peptide or polysaccharide adapted to selectively bind Gal-3, binds to Gal-3 as the blood passes through, showing a measurably reduced amount of Gal-3 after it has passed through the system and is returned to the mammal. Reductions on the order of at least 10%, more effectively 20, 25, 40, 50 or even 60% of circulating Gal-3 may be effected simply by providing more than one module 1008 with Gal-3 binding moieties.

One therapy augmented by the invention disclosed herein is immune cell activation and regulation. As noted, Gal-3 is a mediator of inflammation. Increasing evidence demonstrates, however, that Gal-3 is also an important regulator and modulator of solid tumor environments, and anti-tumor activity. Thus, Gal-3 has been shown to modulate T-cell responses to both non-solid and solid tumors, including pancreatic tumors, through more than one mode of action—including apoptosis, T-cell receptor (TCR) cross-linking and TCR downregulation. Kouo et al, Cancer Immunol. Res., 2015, 3(4): 412-23. Thus, Gal-3 has been found elevated in many solid and non solid-tumor cancers, and appears to support cancer cell survival. Ruvolo, Biochim. Biophys. Acta, 2016, 1863(3):427-37. Accordingly, while activated tumor cell treatment is a recognized anti-cancer treatment, the body's natural mechanisms, including Gal-3 work to offset any treatment gains that might be achieved by immune cell activation.

One method of regulating, augmenting and enhancing immune cell activation in an ex vivo environment is photopheresis. In extracorporeal photopheresis, white blood cells (hereinafter "WBC') are separated out and collected. While only a small fraction of a patient's total WBC are extracted for treatment in any one passage, a patient can go through several rounds of treatment, which is consistent with the timing of apheresis, which permits treatment for a period of hours. In photopheresis, the WBC are mixed with an intercalating agent, such as 8-MOP (methoxsalen) and irradiated with UV light. The WBC are then returned to the body. Using the invention disclosed, this is simply one more module 2008 that the patient's blood or plasma is passed through. The resulting leukocytes are returned to the body. Although these treated cells are more subject to apoptosis than untreated leukocytes, since only a small fraction of the patient's cells are treated in any sitting, their susceptibility to apoptosis alone does not account for the effectiveness of the treatment. It also appears that the treated apoptotic-prone cells are taken up by dendritic cells and macrophages. It is through interaction with the dendritic cell system that the treated cells influence rebalancing of the immune system.

As noted, the body's systems, modulated at least in large measure by Gal-3, tend to limit the impact of photopheresis. Thus, much of the benefit of photopheresis is limited by the tendency of Gal-3 to protect the tumor microenvironment the activated immune cells are to address. Gal-3 also suppresses the immune response and release of cytokines by immune cells. Gal-3 is also frequently a pro-inflammatory driver, which again tends to limit the ability of in vivo blood treatments to impact systemic or localized disorders in the body. Photopheresis is also used in the treatment of a variety of diseases other than T-cell leukemia, including cutaneous T-cell lymphoma and in graft versus host disease. While these treatments are helpful, they are of limited impact because the body's relatively weak or incompetent immune system, often aggravated by inflammation, is unable to capitalize on the advantages provided, because its own system regulates to the contrary.

One example of the tendency of body systems mediated in part by Gal-3 expression is in the role of the development of monocyte-derived dendritic cells, the very cells whose expression is a target of the activated immune cells discussed above. Gal-3 has been shown to be implicated in the induction of a T helper 2 response, but little was known about its interactions. Gal-3 has been shown to induce phosphatidylserine exposure and apoptosis in dendritic cells and their differentiation. Van Stijn et al, Mol. Immunol. 209, 46(16):3292-9. Thus localization and sequestration, possible in a limited sample but difficult systemically, has been show to protect and improve differentiation in dendritic cells.

Figure 3:
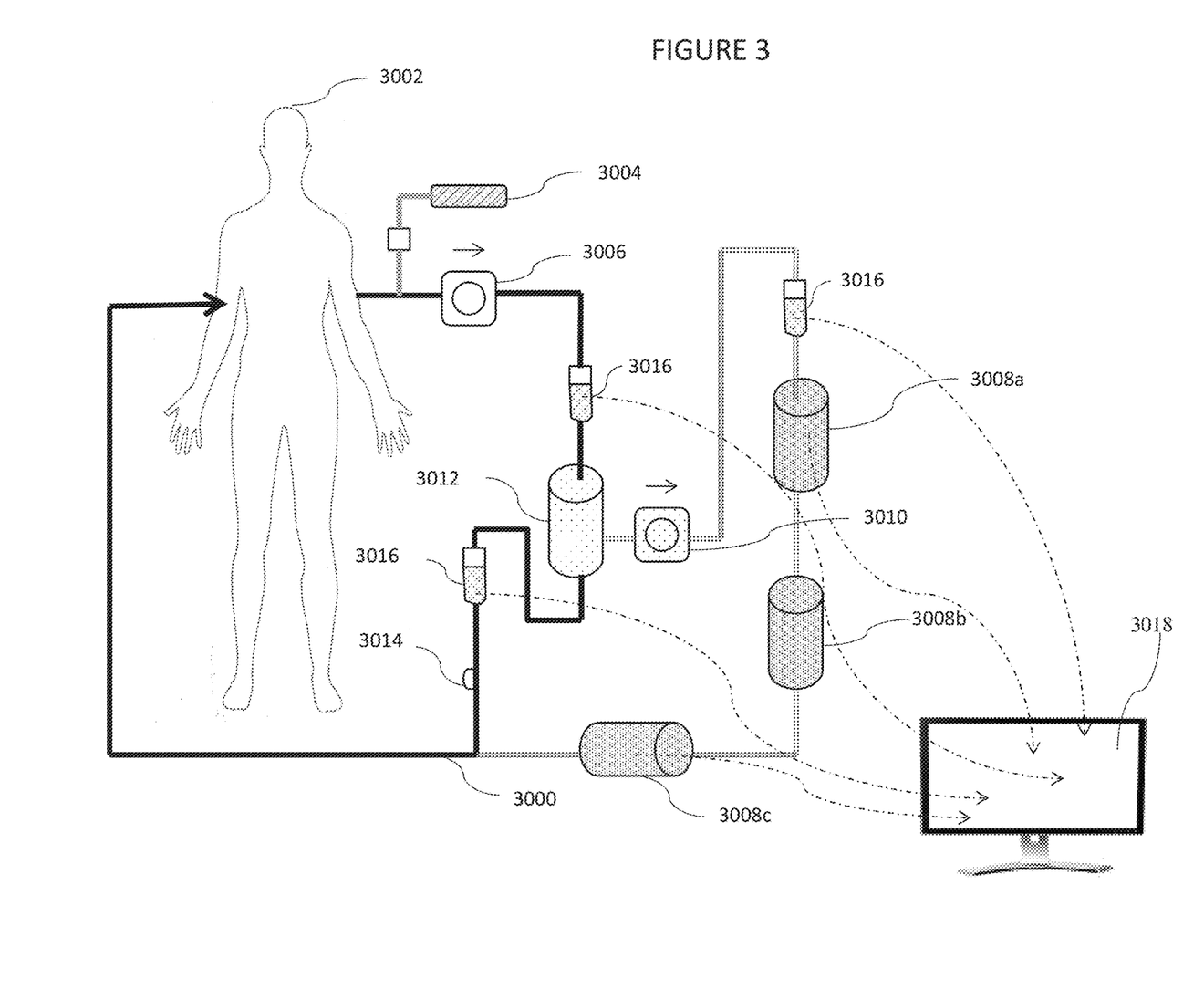
FIG. 3 is a schematic of the inventive device deliberately echoing the structure of FIG. 1, but reflecting the ability of this device to introduce multiple columns and ports to both remove and add a variety of components to the plasma and ultimately the patient.

The invention of this application offers a unique opportunity to combine and maximize the effectiveness of two therapies otherwise limited by the ex vivo nature of the treatment. By employing different modules 3008a, 3008b, 3008c, etc., in any sequence in this invention, the patient may be treated by reduction of significant amounts of circulating Gal-3 while being treated by, e.g., photopheresis—the resulting dendritic-cell uptake and immune cell activation less likely to be defeated by the reduced level of circulating Gal-3. Thus, Gal-3 removal might be effected in modules 3008a and 3008b, while photopheresis is practiced in module 3000c. It is noted that Gal-3 removal can also take place as an independent procedure, preferably in close proximity time wise to photopheresis, and preferably before photopheresis. While it is difficult to measure the presence of synergy in an ex vivo treatment regime, there is clearly an opportunity to enhance the effectiveness of both the reduction of inflammation by Gal-3 removal and the activation of immune cells, particularly through photopheresis, while minimizing the tendency of Gal-3 to undermine the effectiveness of those treatments. One of the greatest problems encountered in many otherwise effective treatments is patient compliance. By combining these treatments in a multi-module process such as the one disclosed herein, multiple regimens are effected in the same time with efficiency, avoiding multiple patient sessions.

To further enhance these and other therapies, the modules employed in the apheresis system of this invention need not be limited to removal and treatment actions. VEGF and TGF-β for example are two well-studied inhibitors of mammalian immune function. Ohm et al, Immunol. Res. 2001, 23(2-3):263-72; Viel et al, Sol. Signal, 2016, 9(415). The art suggests that by addition of signaling receptor blockers, or by adding decoy receptors, the signaling of TGF-β may be limited, reducing the tendency of this agent to promote tumor growth and cancer metastasis. Thus, removal of VEGF, TGF-β and similar CIPFs constitute one aspect of the disclosed invention. By the same measure, their receptors and receptors for Tumor Necrosis Factor (TNF-alpha and beta, primarily) have become targets for therapeutic treatment, the removal or blocking of which is advantageously combined with selective withdrawal of Gal-3. These techniques are advantageously provided in one sitting by Applicant's invention.

At the same time active Gal-3 is removed, soluble TNF receptors, both R-1 and/or R-2 at different ratios based on the condition, are removed, through the same process, by running the plasma fluid over a bed of binding agents of TNF receptors. TNF can then directly target cancer cells or other targets as an effective treatment. The reduction of active Gal-3 in both the circulation and the tissue level will allow TNF to exert its beneficial effects with a reduced amount of inflammation and fibrosis which limits its use. Wu et al, Arch. Dermatol. 20:1-7 (2012). The effective removal of serum Gal-3 also enhances chemotherapy, particularly, but not exclusively, when combined with TNF receptor removal. This can be further combined with the administration, through the same modules, of TNF receptor inhibitors and ligands, which further improve, systemically, the ability of TNF to target tumors, preferably aided by the removal of Gal-3. The removal of TNF receptors, and addition of TNF receptor binders, might be effectively provided for in modulus 3008y and 3008z.

As illustrated above, the modules that are combined into the apheresis system may be adapted to address the particular challenges presented for any particular patient. The ability to "print" columns provided with the necessary functionality coupled with the ease with which functional agents may be added to the same withdrawn blood or separated plasma permit adaptation of the methods and system of this invention to any given patient's needs. As noted, in a single patient visit, targets such as a galectin, including Gal-3, TNF alpha and beta receptors, cytokines of various character may all be removed. In some patients, excessive TNF may be removed by providing a column with specialized receptors. At the same time, it may be possible to add agents whose effectiveness is enhanced by removal of inhibiting agents. Thus, where other CIPF's, inflammatory compounds, growth factors, etc. are removed, it may be advantageous in the same treatment to add agents, such as various pharmaceuticals and similar therapeutic agents, like chemotherapeutic agents, hormones, CAR-T Cells, etc. As noted above, the invention embraces the sensitization of various cells, in a variety of modes such as activated immune cells. Both host and donor cells may be involved. Those of skill in the art—medical doctors with familiarity with the cascade of problems presented by a single or multiple health issue, will select those treatments best suited to address a patient's needs in a single, comfortable setting. Improving patient compliance is just one aspect of the improvements obtained by this invention.

This invention has been disclosed in terms of embodiments and alternatives readily identifiable to the inventor today. It goes without saying that the pace of medical advance is such that tomorrow, new targets for removal will be identified, new agents for addition will be advanced, and new technologies for the design and manufacture of personalized option will become manifest. The essential character of this invention is rather than relying on apheresis for the high cost treatment of a few diseases or syndromes, it may be used to tailor superior solutions on a patient-by-patient basis without introducing extraordinary costs or delays of heroic proportions in terms of approvals. By providing an apheresis device that may be personalized by switching in or out a column or cartridge, custom made or specifically prepared for the patient's needs, recognizing that in many if not most cases those needs persist over time, the fundamental cost of apheresis can be defrayed and its advantages employed in the treatment of a wide-variety of conditions not previously adequately addressed by conventional options, and a more effective therapy can be offered.

What is claimed is:

1. A method for treating a mammal in an ex vivo system, comprising:
   withdrawing an amount of blood from said mammal and introducing it into an ex vivo treatment system, wherein said system comprises at least two modules, wherein each of said modules is intended to modify the composition of said blood extracorporally before returning said withdrawn blood to said patient;
   wherein at least one of said modules selectively withdraws at least ten percent of galectin-3 in said withdrawn blood by passing said blood through a module provided with a moiety which selectively binds galectin-3 selected from the group consisting of an antibody, antibody fragment, non-antibody peptides, each of which selectively binds galectin-3, a polysaccharide which selectively binds galectin-3, or a combination thereof;

wherein at least one of said modules treats said withdrawn blood with photopheresis to expose white blood cells in withdrawn blood to ultraviolet irradiation to render said white blood cells more susceptible to apoptosis upon return to the body and uptake by dendritic cells; and returning said withdrawn blood, comprising said blood with reduced galectin-3 content and ultraviolet irradiated white blood cells to said patient together with remaining blood components, wherein said process of removal of blood, treatment and return is continuous;

wherein in one of said modules agents which bind TNF receptors such that said bound receptors are not able to bind with TNF in said mammal are introduced into said withdrawn blood prior to its return to the mammal.

2. The method of claim 1, wherein said method further comprises removing TNF receptors from said withdrawn blood.

3. The method of claim 1, wherein said withdrawn blood is separated into plasma and cellular components prior to introduction of said withdrawn blood into the first of said modules such that treatment in said modules comprises treatment of plasma.

4. An ex vivo system for treatment of blood of a mammal through apheresis, comprising:

a channel through which blood is withdrawn from said mammal and introduced into said system;

at least one module through which said withdrawn blood is directed which comprises a passage for said blood and an agent which selectively binds galectin-3 selected, at least one module for photopheresis of white blood cells present in said blood withdrawn from said mammal so as to expose said white blood cells to ultraviolet irradiation to render said irradiated white blood cells more susceptible to apoptosis and uptake by dendritic cells on return to said mammal, wherein said photopheresis module is upstream or downstream of said galectin-3 binding module, and a channel for return of said withdrawn blood, having been treated to withdraw galectin-3 and irradiate said white blood cells, to said patient, wherein said system provides for withdrawal of said blood, passage of said blood through said modules and return to said patient continuously while the patient is treated;

wherein said system comprises a module in which active agents comprising at least moieties which bind TNF receptors in vivo are introduced into said withdrawn blood prior to return of said blood to said mammal.

5. The system of claim 4, wherein said system further comprises a module wherein TNF receptors and blocking agents are removed from said withdrawn blood, wherein said module is upstream or downstream of said modules for photopheresis and galectin-3 removal, and said withdrawn blood is directed through said module for TNF receptor removal prior to return to said mammal.

6. The system of claim 4, wherein said system comprises a filter for the separation of plasma and cellular components of said withdrawn blood, wherein said filter is upstream of all said modules and said withdrawn blood is introduced thereto.

* * * * *